US005635396A

United States Patent [19]
Fedun

[11] Patent Number: 5,635,396
[45] Date of Patent: Jun. 3, 1997

[54] COVERSLIP HOLDER

[75] Inventor: Oresta N. Fedun, Wanaque, N.J.

[73] Assignee: Becton, Dickinson and Company, Franklin Lakes, N.J.

[21] Appl. No.: 521,485

[22] Filed: Aug. 30, 1995

[51] Int. Cl.$^6$ .............................. C12M 3/04; C12M 1/14
[52] U.S. Cl. .................... 435/283.1; 435/288.3; 435/305.1; 435/809
[58] Field of Search ............................ 435/283.1, 288.3, 435/288.7, 289.1, 305.1, 305.4, 809; 422/99, 104

[56] References Cited

U.S. PATENT DOCUMENTS

| | | | |
|---|---|---|---|
| 3,065,150 | 11/1962 | Kravitz | 435/305.1 |
| 4,446,234 | 5/1984 | Russo et al. | 435/297.2 |
| 4,608,342 | 8/1986 | Nees | 435/297.5 |
| 4,917,793 | 4/1990 | Pitt et al. | 435/297.1 |
| 5,190,878 | 3/1993 | Wilhelm | 435/297.2 |
| 5,468,638 | 11/1995 | Barker et al. | 435/304.1 |

OTHER PUBLICATIONS

*Culturing Nerve Cells*, G. Banker and K. Goslin, MIT Press, (1991), 255–259.

*An electron Microscopic Analysis of Hippocampal Neurons Developing in Culture: Early Stages in the Emergence of Polarity*, The Journal of Neuroscience, Oct. 1993, 13(10): 4301–4315.

*Preferential Dendritica Localization of Pericentriolar Material in Hippocampal Pyramidal Neurons in Culture*, Cell Motility and the Cytoskeleton 25:336–344 (1993).

Primary Examiner—William H. Beisner
Attorney, Agent, or Firm—Arthur D. Dawson

[57] ABSTRACT

A holder useful for supporting a coverslip above the bottom surface of a vessel includes a lower portion with a surface for supporting a coverslip and an upper portion with at least one protuberance. The holder has an opening intermediate the lower portion and the protuberance for receiving the coverslip.

8 Claims, 8 Drawing Sheets

COVERSLIP HOLDER

FIELD OF THE INVENTION

The present invention generally relates to cell culture devices and more particularly to culturing cells on a coverslip.

BACKGROUND

In biological research, small scale cell culture is often conducted on the surface of microscope slide coverslips. Coverslips are readily available, easily cleaned and uniform. Coverslips are commonly made from glass and plastic. The coverslips are available as circles with diameters of 12 millimeters (mm) and 18 mm, squares with 18 mm, 22mm and 25 mm sides and rectangles dimensioned from 11 mm by 22 mm to 48 mm by 60 mm. When used for cell culture, the coverslips are generally cleaned, often coated with protein, dried and placed in a culture vessel having a flat bottom. The culture vessels used for these procedures are either Petri dishes, where several coverslips may be placed at one time, spaced apart from each other, or a multi-well plate where each coverslip is placed in an individual well.

A reference text entitled, *Culturing Nerve Cells*, G. Banker and K. Goslin, MIT Press, (1991) discusses the use of coverslips for cell culture. In the reference, the use of coverslips is reported in a "Protocol for Preparing Low-Density Hippocampal Cultures" on pages 255–259. The "protocol" reports that it is difficult to apply microscopic techniques to cells grown directly in plastic culture dishes. The "protocol" suggests plating hippocampal cells onto glass coverslips treated with a protein, polylysine, to enhance cell adhesion.

According to the "protocol," to conduct a cell monoculture, i.e., growing only one type of cells, protein coated coverslips are placed flat on the bottom of a container, generally a Petri dish or a well of a multiwell plate, and a cell suspension in an aqueous medium is added to the container. The container with the coverslip and the suspension is incubated to develop a substantially confluent monolayer of the cells on the coverslip. For microscopic analysis of the cells or for further treatment of the cells, the coverslip with the monolayer of cells generally must be removed from the container with forceps. Since both the coverslip and the container bottoms are substantially flat, the aqueous medium often causes the coverslip to adhere strongly to the bottom of the container. Because of this adhesion, handling the coverslip with forceps often cracks the coverslip, disrupts the cells and may render the cells on the coverslip useless for further work.

When a cell co-culture is conducted, i.e., growing cells of a first type in close proximity to cells of a second type so that they interact chemically without direct contact, the coverslip and container technique also is useful. In the "protocol" from the reference *Culturing Nerve Cells*, the authors suggest applying small dots of wax to the edges of a coverslip prior to coating the coverslip with protein. To prepare a co-culture according to the "protocol," cells of a first type are cultured on the coverslip, on the side with the wax dots, following the mono-culture procedure to a confluent monolayer. The need to culture the first type cells on the side of the coverslip with the wax dots continues the possibility that some coverslips may crack in the handling necessary for the next step. Then, the coverslip with the first type cells is removed from its original container and placed in a second container with a confluent monolayer of cells of a second type cultured on its bottom surface so that the coverslip side having the first type cells faces the second type cells in the second container. In the placement of the coverslip in the second container, the wax dots support the coverslip with the first type of cells on the surface in close proximity to the cells of the second type. In this co-culture application using coverslips, the wax dots provide a separation between the coverslip and the container bottom. In addition to allowing the co-culture to proceed without direct contact between the cells, the wax dots allow the coverslip to be easily picked up and manipulated with forceps by substantially preventing adherence of the coverslip to the bottom of the container.

The addition of wax dots to a coverslip, while providing a separation between the coverslip and the container bottom, is time consuming and technique sensitive. Additionally, the wax dots are a potential source of contamination and may come off during handling. If a coverslip holder was available that would support a coverslip above the bottom of a vessel, the, efficiency and effectiveness of laboratory work in cell mono-culture and co-culture would be. enhanced. Such a holder is described below.

SUMMARY

A holder of the present invention useful for supporting a coverslip above a surface of a vessel includes a lower portion with a surface for supporting the coverslip and an upper portion with at least one protuberance. The holder has an opening intermediate to the lower portion and the protuberance for receiving the coverslip.

The coverslip holder of the present invention enables laboratory workers who use coverslips as surfaces for culturing cells to improve the efficiency of their efforts by supporting the coverslip above a surface of a vessel and substantially reducing the adherence of a coverslip to the vessel bottom. The holder allows the worker to easily manipulate the coverslip, substantially reducing breakage of coverslips and disruption of growing cells during handling or transfer of the coverslips from one vessel to another. Additionally, the holder allows the workers to continue to utilize their current procedures and equipment substantially unchanged while providing the fragile coverslips with a support to facilitate handling. The coverslip holder of the invention allows substantially unimpeded usage of standard microscopic study techniques and is easily removable from the coverslip for any subsequent steps in a procedure.

DETAILED DESCRIPTION

While this invention is satisfied by embodiments in many different forms, there is shown in the drawings and herein described, several embodiments of the invention with the understanding that the present disclosure is to be considered descriptive of the principles of the present invention and is not intended to limit the scope of the invention to the embodiments illustrated. The scope of the invention is measured by the appended claims and their equivalents.

Referring to FIGS. 1–6, a coverslip holder 10 of the present invention has a lower portion 12 with a surface 14 for supporting a coverslip 20. Holder 10 has an upper portion 22 with at least one protuberance 24. Holder 10 has an opening 28 intermediate upper portion 22 at protuberance 24 and lower portion 12 for receiving coverslip 20.

Figure 1:
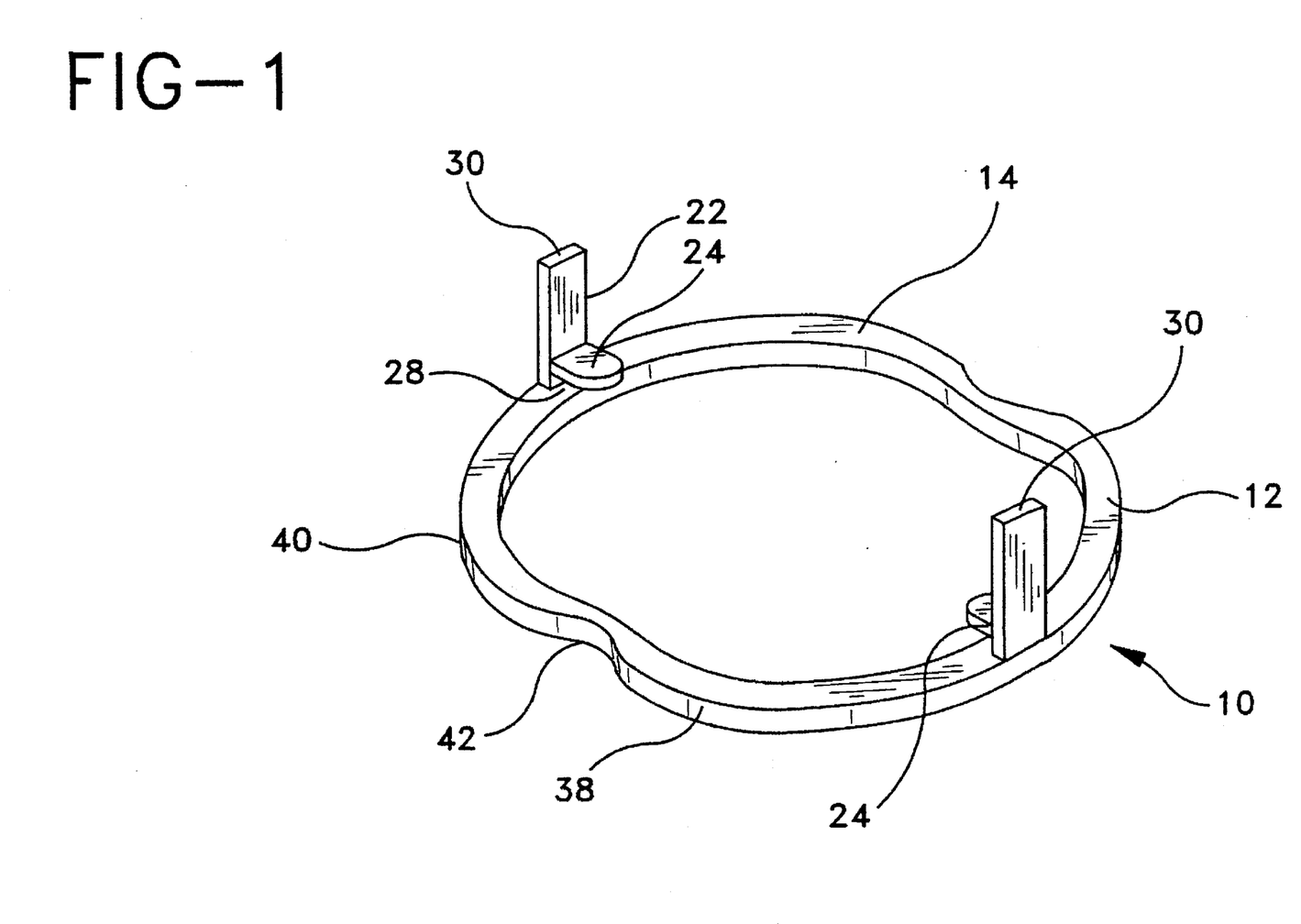
FIG. 1 is a perspective view of a coverslip holder of the present invention.
Figure 2:
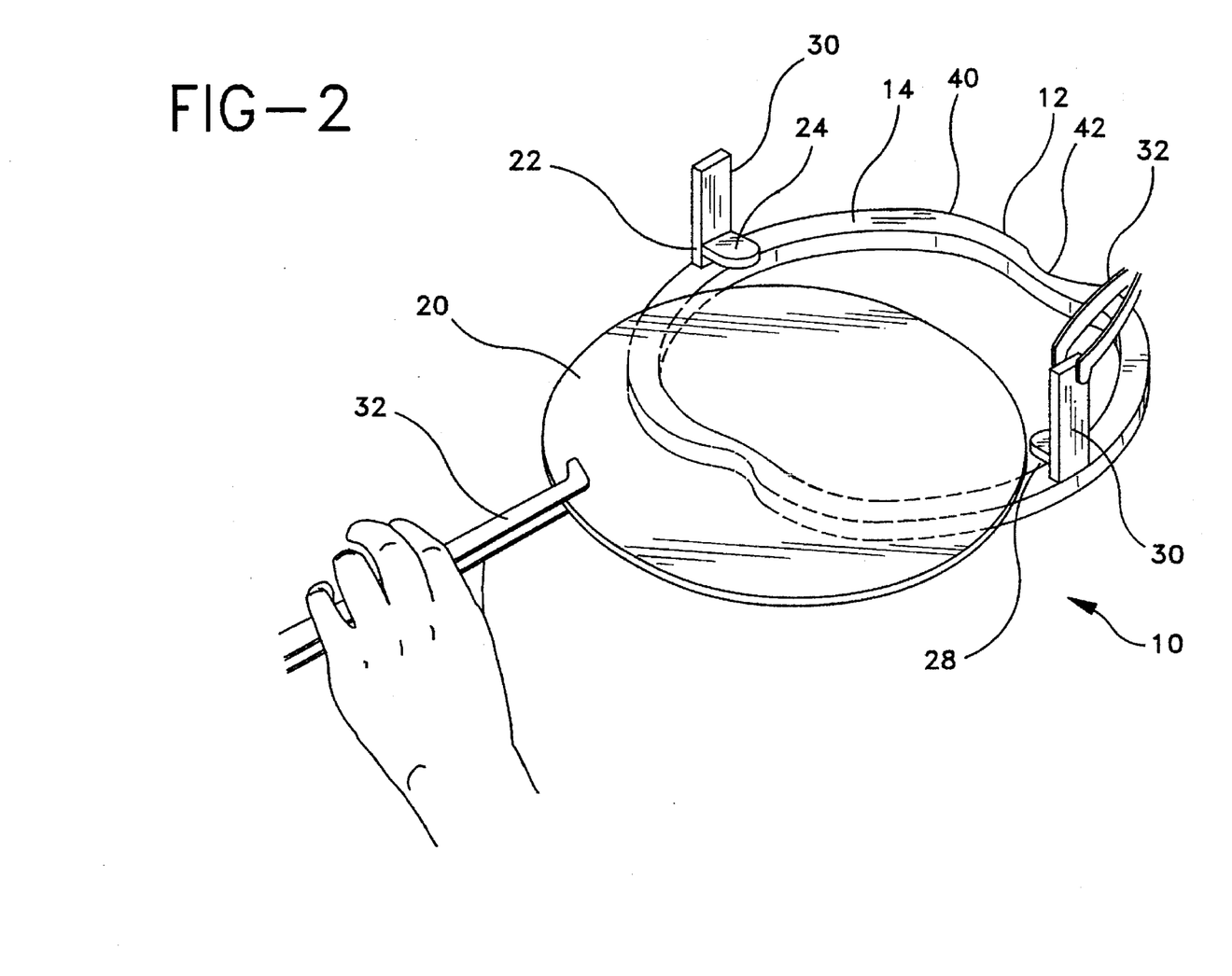
FIG. 2 is a perspective view of the invention of FIG. 1 showing a circular coverslip partially fitted therein.

Preferably, upper portion 22 includes at least one tab 30 extending upwardly to facilitate handling the holder with a pair of forceps 32 or similar laboratory handling devices. FIG. 2 shows holder 10 with circular coverslip 20 partially fitted into opening 28.

Figure 3:
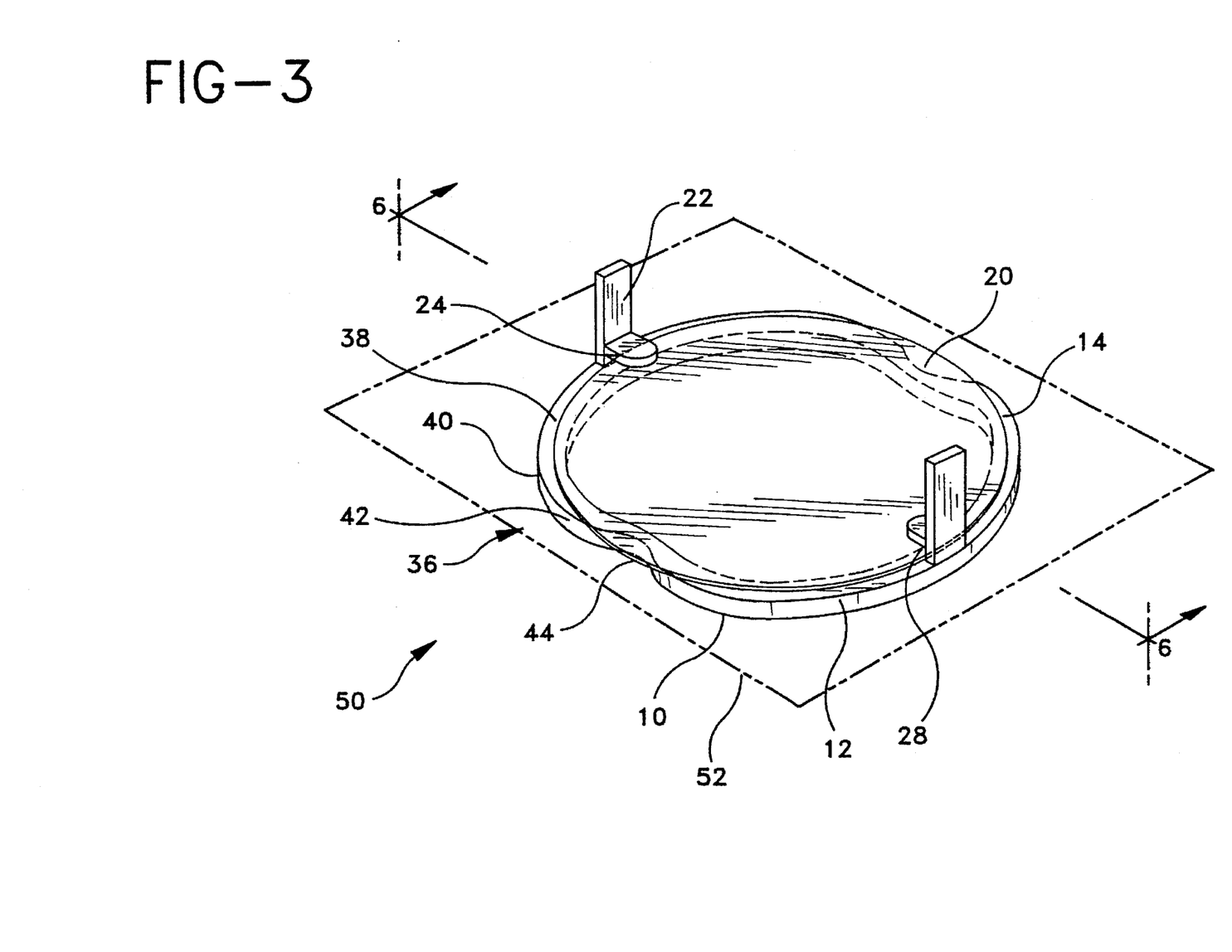
FIG. 3 is a perspective view of the invention of FIGS. 1 and 2 showing the coverslip fitted therein.
Figure 5:
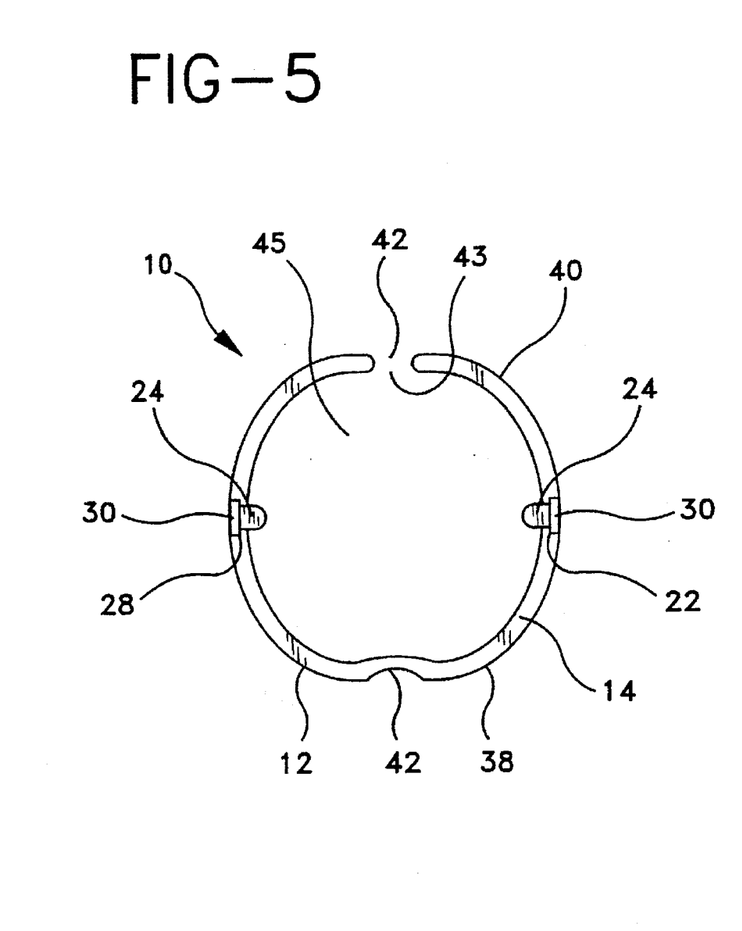
FIG. 5 is a top plan view of the invention of FIG. 1.

FIG. 3 illustrates holder 10 with circular coverslip 20 fully mounted forming an assembly 36. Preferably, lower portion 12 of the holder is in the general form of an annulus 38 having a perimeter 40. For particular applications, other shapes for lower portion 12 also are considered within the scope of the invention. In order to facilitate handling of coverslip 20 with forceps when it is being placed into or being removed from the holder, surface 14 preferably includes at least one recess 42 open from perimeter 40. Preferred recess 42 provides a portion 44 of coverslip 20 that is unsupported by surface 14. Portion 44 thus projects beyond the lower portion providing direct access to coverslip 20 for manipulation by forceps 32 or other laboratory manipulation instruments. For particular applications, as shown in FIG. 5, at least one recess 42 may include a passage or an open segment 43 for providing fluid communication to an area 45 contained within the lower portion when coverslip 20 is mounted in the holder and the assembly is in a vessel.

Figure 4:
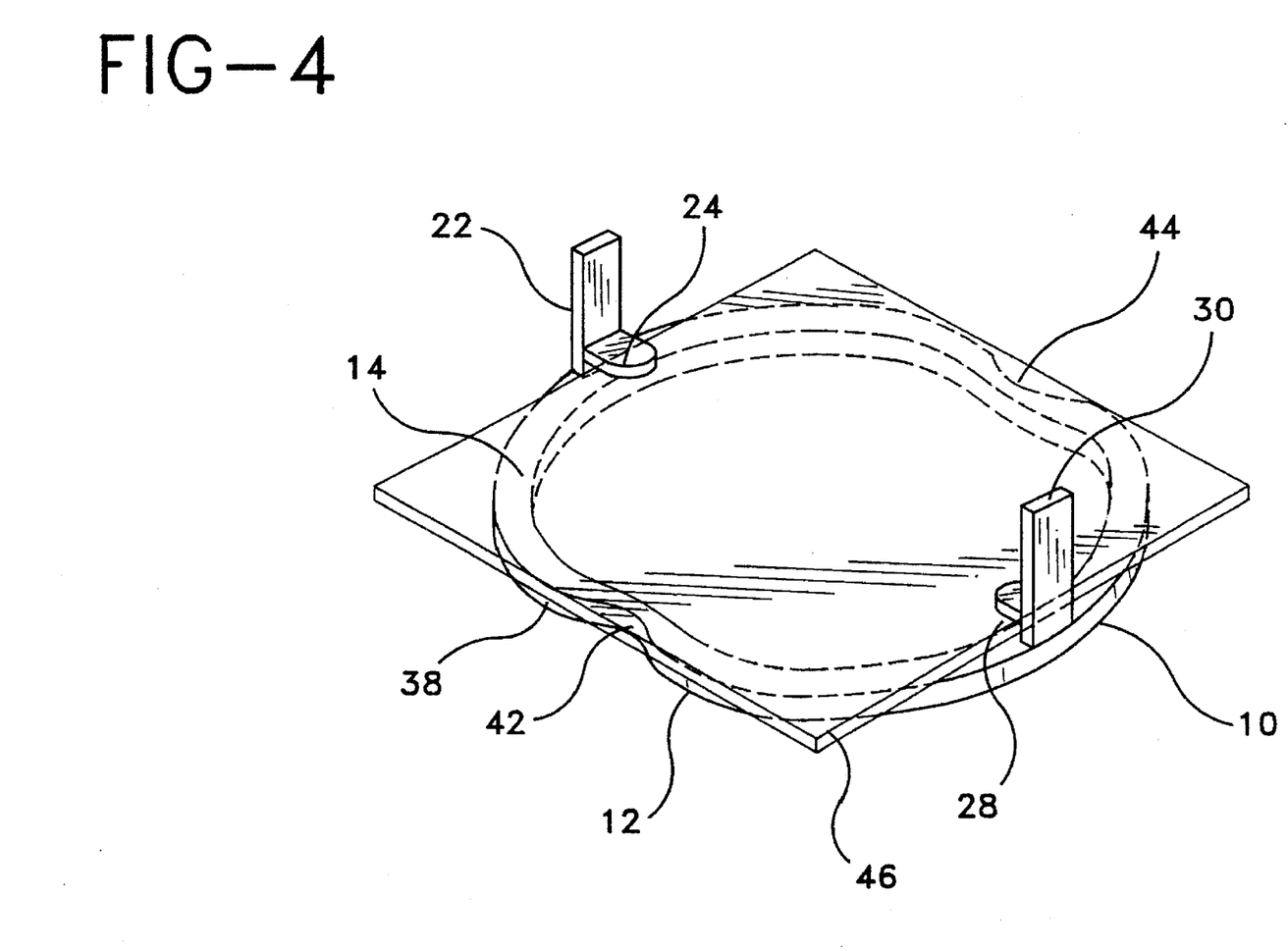
FIG. 4 is perspective view of the invention of FIG. 1, analogous to the view of FIG. 3, showing the invention with a square coverslip fitted therein.

To simplify this description, coverslip 20 is generally shown having a circular shape. One skilled in the art recognizes that coverslips are also commercially available as square, rectangular or other shapes. A square shaped coverslip 46 is shown mounted in holder 10 in FIG. 4. When FIG. 4 is studied, it is apparent that the holder of the invention is suitable for holding square and rectangular coverslips as well as the generally illustrated circular shape. Thus, the scope of the invention includes the use of square, rectangular or other shaped coverslips as well as the generally illustrated circular coverslips.

Figure 6:
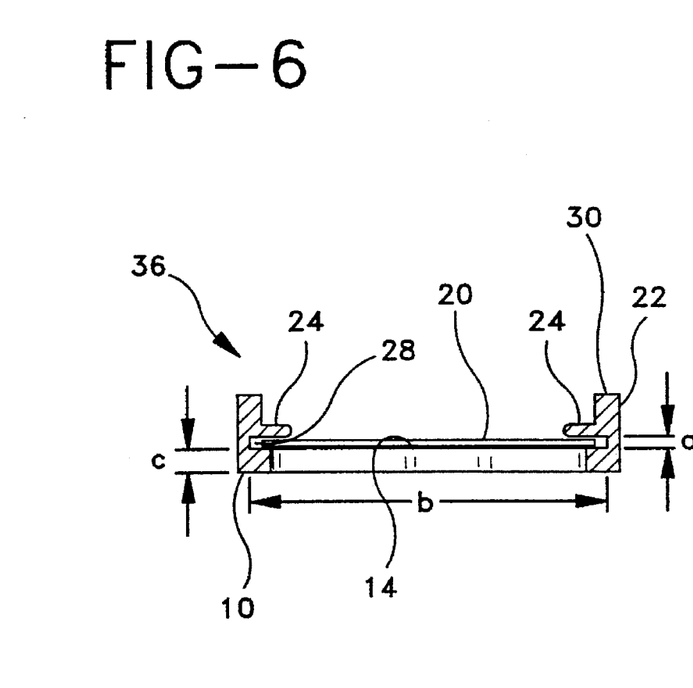
FIG. 6 is a cross sectional view of the invention of FIG. 3 taken along the line 6—6.

Coverslips are generally glass and are commercially available in thicknesses from about 0.09 mm to about 0.32 mm. Coverslips generally are produced as circles with diameters about 12 mm, 18mm, 22 mm and 25 mm; as squares with 18 mm, 22 mm and 25 mm sides and as rectangles with sides ranging from 11 mm by 22 mm to 48 mm by 60 mm. Other sizes are within the purview of this invention. The cross sectional view of preferred assembly 36 seen in FIG. 6 illustrates opening 28 and tabs 30. Preferably, opening 28 has a dimension "a" sized to accept the thickness of the coverslip with an interference fit so that the coverslip is releasably retained in the holder. Preferably, a width dimension "b" of opening 28 is sized to accept the width dimensions of the coverslip with a clearance so that the coverslip is easily installed and removed from the holder. Preferably, coverslip 20 is compatibly sized with holder 10 so that coverslip 20 is releasably retained in the holder.

Additionally, since some of the commercially available sizes of coverslips are not easily distinguished from one another, e.g., 18 mm diameter from 22 mm diameter, preferably, a color code scheme is used to identify holders as suited for accepting a particular size coverslip. As an example of the color code, red indicates a holder for a 12 mm coverslip, blue indicates a holder for an 18 mm coverslip, yellow indicates a holder for a 22 mm coverslip and green indicates a holder for a 25 mm coverslip. Numerous color or identification schemes are possible for the holders and are considered within the scope of the invention.

Preferably, the holder of the present invention is formed from a thermoplastic material with a density greater than one to substantially reduce buoyancy of the holder coverslip assembly when aqueous media and cell suspensions are added to a vessel containing the assembly. Suitable thermoplastic materials include, but are not limited to, polycarbonate, polyethylene, polypropylene, polystyrene, and the like compounded with fillers to increase the density of the material. The fillers may be used to impart the color code to the material. Preferably, the filler or colorant used is non-leachable into aqueous media and not toxic to cells.

Assembly 36 of the present invention including holder 10 and compatibly sized coverslip 20 is preferably supplied as a packaged unit 50. When supplied as a unit, assembly 36 is preferably sealed in a package 52, illustrated in phantom in FIG. 3, formed from materials substantially resistant to the passage of microorganisms and exposed to conditions rendering any microorganisms present in the package non-viable. Suitable packaging materials include, but are not limited to, paper, non-wovens, polymeric sheet, polymeric films and combinations thereof. Suitable conditions for rendering any microorganisms non-viable include, but are not limited to, exposure to gaseous sterilants such as ethylene oxide and the like, and ionizing radiation such as gamma and electron beam. After the exposure, the preferred packaged assembly is considered sterile until the package is opened.

Many cells form confluent monolayers on clean glass surfaces coated with protein. Glass coverslips are widely available and quite uniform. To form a cell mono-culture as described in the background, cleaned glass coverslips are coated with protein, often polylysine, allowed to dry and placed in a laboratory culture vessel, often a flat circular open dish with straight sidewalls having a flat bottom commonly called a Petri dish. A suspension of cells in a suitable, generally aqueous, medium is then introduced into the dish. The dish with the suspension is then incubated until a confluent layer of cells develops on the coverslip. The coverslip is then removed from the vessel, generally with forceps, and the desired analysis conducted, often a microscopic analysis. Since both the coverslip and the vessel bottom surface both are substantially flat, the coverslips with the confluent layer of cells often are quite difficult to lift from the surface because of surface tension effects of the aqueous medium between the coverslip and the bottom surface. Often the confluent cell layer is disrupted or the coverslip broken in manipulations with forceps rendering the culture substantially useless for subsequent work.

Figure 7:
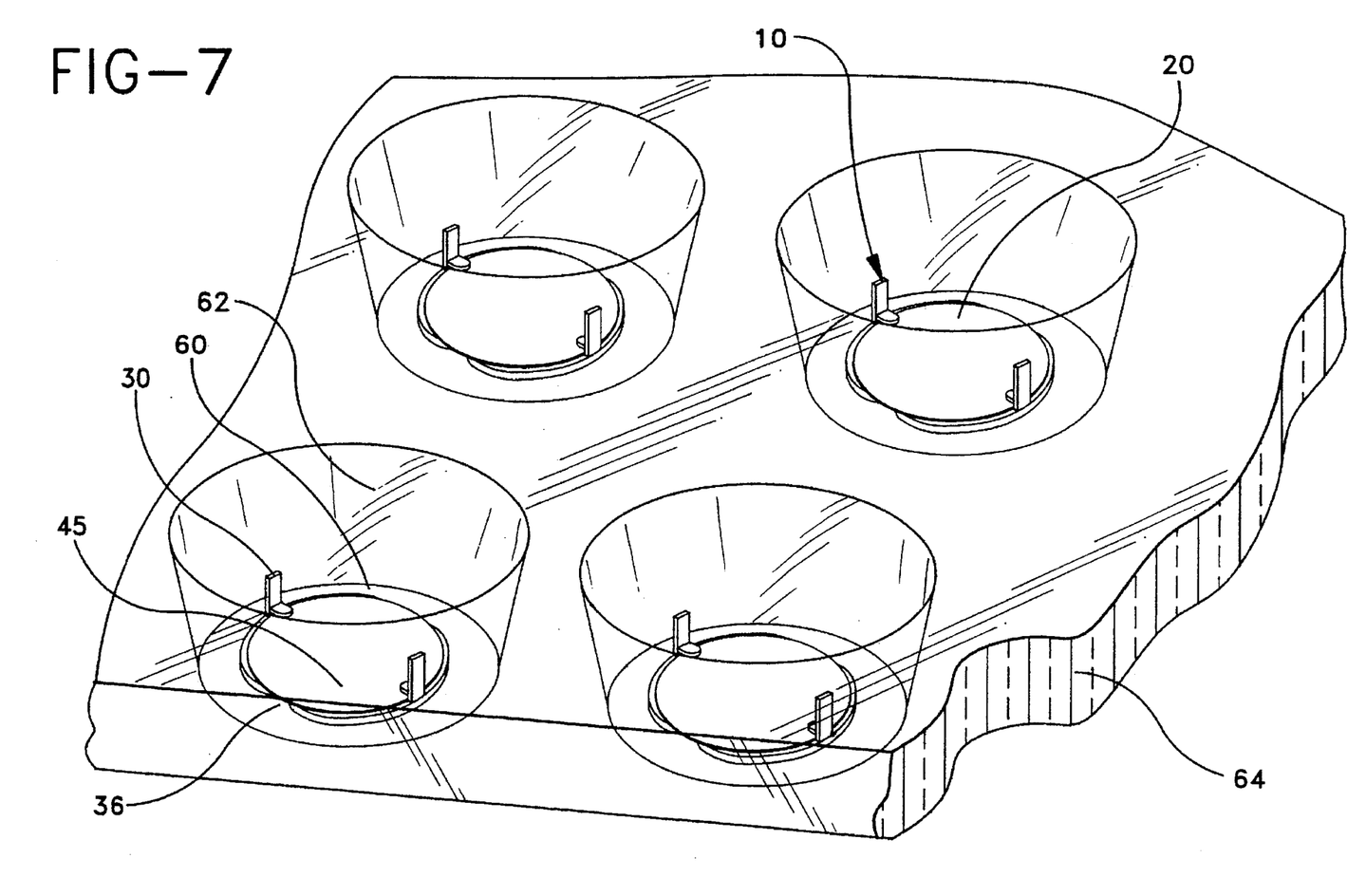
FIG. 7 is a perspective view of a well of a multiwell plate with a coverslip in a holder of the present invention, as shown in FIG. 3, placed therein.
Figure 8:
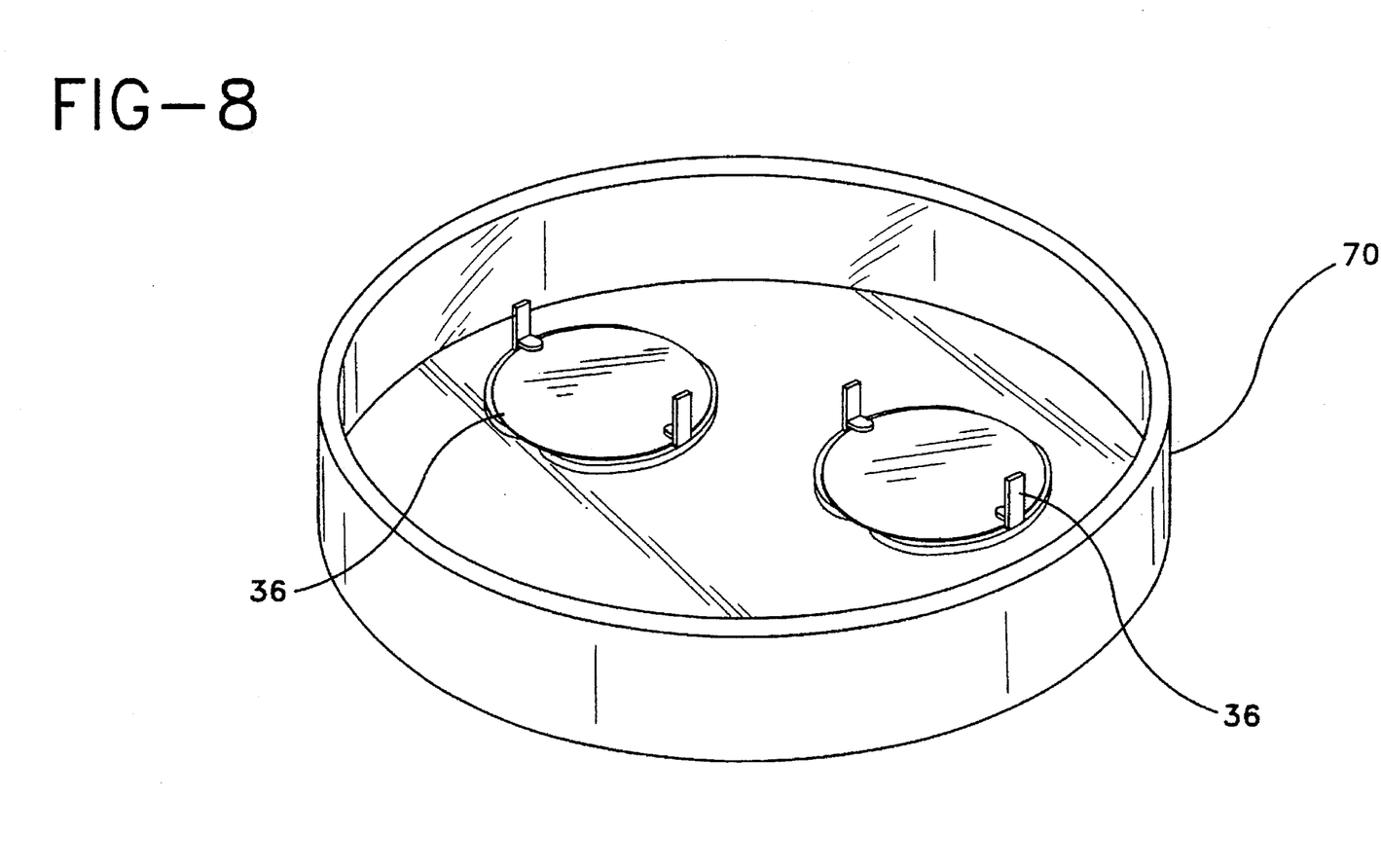
FIG. 8 is a perspective view of a Petri dish with two coverslips in holders of the present invention, as shown in FIG. 3, placed therein.

To conduct a similar cell mono-culture using preferred assembly 36 of the present invention, preferred holder 10 supports coverslip 20 above and substantially parallel to the laboratory vessel bottom. Referring to FIG. 7, assembly 36 is placed on a bottom surface 60 of a well 62 of a multiwell plate 64 and a suspension of cells in medium is added in similar fashion to the procedure described above. When the laboratory worker needs to manipulate the coverslip with forceps, the forceps are applied to preferred tab 30 and the holder with the coverslip is lifted from the vessel. Holder 10 supports coverslip 20 above bottom surface 60 (in FIG. 6, a distance "c") substantially reducing adhesion between coverslip 20 and the bottom surface of the vessel, because holder 10 supports coverslip 20 above and substantially parallel to the bottom surface. Holder 10 thus allows the coverslip in the holder to be easily removed for analysis. FIG. 8 shows two examples of assembly 36 in a Petri dish 70.

Figure 9:
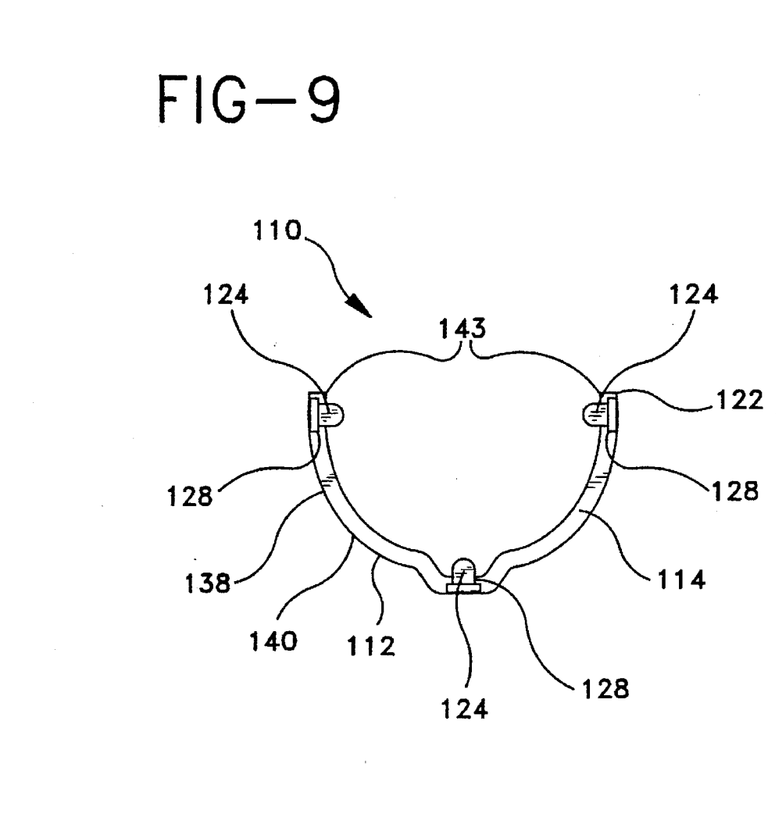
FIG. 9 is a top plan view, analogous to the view of FIG. 5, of an alternative embodiment of the invention of FIG. 1.
Figure 10:
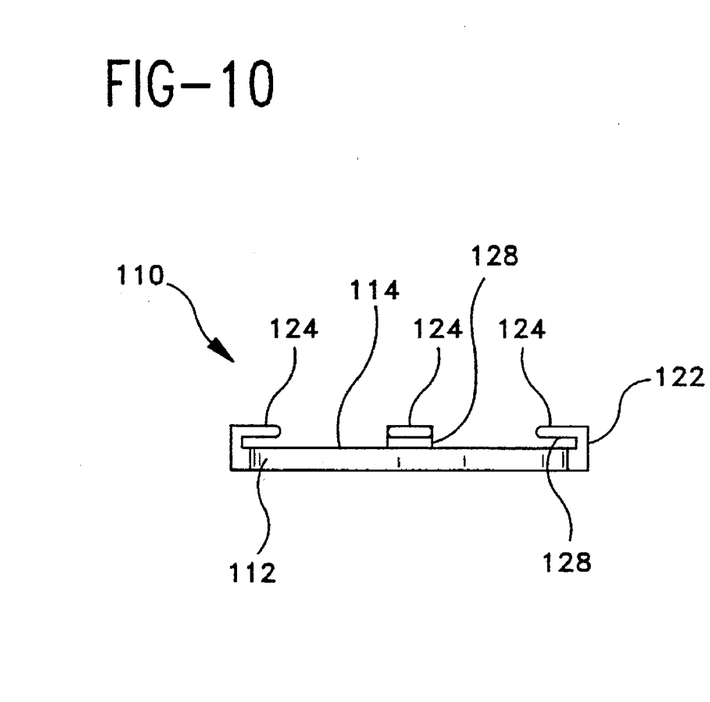
FIG. 10 is a side elevation view, as seen from the open side, of the embodiment of FIG. 9.

FIGS. 9 and 10 show an alternate embodiment of the present invention. In this embodiment, the structure of the holder is substantially similar to the holder of FIGS. 1–6, Accordingly, substantially similar components performing substantially similar functions are numbered identically to those components of the embodiment of FIGS. 1–6 except that the reference characters include "hundreds" digits to identify those components in FIGS. 9 and 10. Holder 110 has a lower portion 112 with a surface 114 for supporting a coverslip. Holder 110 has an upper portion 122 with at least three protuberances 124. Holder 110 has at least three openings 128 intermediate upper portion 122 and lower portion 112 at protuberances 124 for receiving the coverslip. In this embodiment, lower portion 122 is in the general form of an annulus 138 having a perimeter 140 with open segment 143 occupying between about one half and one third of perimeter 140. Open segment 143 allows a coverslip to be mounted and dismounted from holder 110 without scraping most of the contact surface of the coverslip over surface 114 of the holder. Additionally, as seen in FIG. 10, holder 110 does not have any upwardly projecting tabs for handling, seen in the embodiment of FIGS. 1–6. Further, holder 110 can support a coverslip with a first side and a second side in a first position with the first side facing the bottom of the vessel and in a second position with the second side facing the bottom of the vessel by resting on protuberances 124, making the holder suitable for use in co-culture applications. Holder 110 also allows free exchange of fluid between the area within and without the area enclosed by lower portion 122 through open segment 143 when the holder is fitted with a coverslip and placed on the bottom of a vessel.

In the example of a co-culture procedure cited above in the background, *Culturing Nerve Cells*, Banker and Goslin, MIT Press, (1991), the cited protocol gives a method for preparing a hippocampal neuron culture in the presence of glial cells using coverslips and culture vessels. The cited protocol describes applying wax beads to coverslips to support the coverslips above the surface of the vessel. To conduct a similar co-culture using a coverslip in holder 110 of the present invention, a coverslip is fitted into the holder and coated with polylysine as is done in the protocol. The use of holder 110 eliminates the need for the operator to add wax beads to the coverslip. In the co-culture of neurons in the presence of glial cells, a laboratory worker prepares a confluent layer of glial cells on bottom surface of a culture vessel. The neurons are concurrently cultured in another vessel on the first (upward facing) surface of a coverslip mounted in holder 110 in a similar fashion as that described above for the mono-culture. During the development of the neurons on the first surface of the coverslip, holder 110 substantially prevents the adherence of the coverslip to the neuron vessel as described for the mono-culture. Then the coverslip with the neurons on the first surface is transferred to the vessel with the glial cells on its bottom surface and placed with the neuron covered first surface facing the confluent layer of glial cells on the vessel bottom supported by the protuberances. A suitable medium is then added and the vessel incubated for the co-culture portion of the protocol. Holder 110 supports the neuron covered coverslip above and substantially parallel to the bottom surface of the receptacle by resting on the protuberances, in close proximity to the glial cells, but substantially without direct contact between the neurons on the coverslip and the glial cells on the receptacle bottom surface. Thus, by use of holder 110 of the present invention, the laboratory worker can concentrate attention on the techniques of cell culture manipulations and the analysis of the cells. The laboratory worker does not have to spend time developing and practicing the technique of applying wax droplets to coverslips, substantially reducing the time necessary to get to the actual co-culture of the cells and increasing the efficiency of the laboratory. Holder 110 allows removal of the coverslip from the holder substantially without disruption of cells on either the first or the second surface of the coverslip for further study.

The coverslip holder of the present invention enables laboratory workers that use coverslips as surfaces for culturing cells to improve the efficiency of their efforts by supporting the coverslip above a surface of a vessel and substantially reducing the adherence of a coverslip to the vessel bottom. The holder is useful in both mono-culture and co-culture applications. The invention allows the workers to continue to utilize their current procedures and equipment substantially unchanged while providing the fragile coverslips with a support to facilitate handling. The coverslip holder of the invention allows substantially unimpeded usage of standard microscopic study techniques such as microscopic observation and manipulation such as microinjection. The holder is easily removable from the coverslip for any subsequent steps in a procedure substantially without disruption of cells grown on the surface of the coverslip.

What is claimed is:

1. A holder for supporting a coverslip above a surface of a vessel comprising:
    an upper portion including at least one protuberance and having at least one tab projecting upwardly for manipulating said holder;
    a lower portion having a surface for supporting a coverslip; said lower portion comprising a substantially planar annulus with a perimeter having at least one recess therein so that at least a portion of the coverslip received by said holder is unsupported and projects beyond said annulus thereby providing access to the coverslip for manipulation; and
    an opening intermediate said lower portion and said protuberance for receiving the coverslip.

2. The holder of claim 1 wherein said lower portion further comprises at least one passage for providing fluid communication therethrough to an area contained within said lower portion to outside said lower portion when the coverslip is mounted in said opening and said holder is placed in a vessel.

3. The holder of claim 2 wherein said passage comprises an open segment in said lower portion.

4. The holder of claim 3 wherein said open segment comprises less than about one half of said lower portion and said upper portion further includes at least three protuberances so that said holder supports the coverslip having a first side and a second side in a first position with said first side facing the bottom of the vessel and a second position with said second side facing the bottom of the vessel.

5. The holder of claim 1, wherein said opening is sized to accept a preselected thickness of the coverslip with an interference fit thereby releasably retaining the coverslip in said holder.

6. The holder of claim 5 wherein said holder further comprises means for identifying a preselected size of the coverslip to be fit in said opening.

7. The holder of claim 6 wherein said means for identifying said size comprises a color code scheme having an assigned color for each preselected coverslip size.

8. A holder for supporting a coverslip above a bottom of a vessel comprising:

a lower portion with a surface for supporting a coverslip and having a generally annular shape and a perimeter with at least one recess therein;

an upper portion comprising a plurality of protuberances and a plurality tabs projecting upwardly; and said holder having an opening intermediate said lower portion and said protuberances for receiving a coverslip.

* * * * *